United States Patent [19]

Duhamel et al.

[11] Patent Number: 4,788,344
[45] Date of Patent: Nov. 29, 1988

[54] PROCESS FOR THE PREPARATION OF POLYENE ETHERS

[75] Inventors: Lucette Duhamel; Pierre Duhamel, both of Mont-Saint Aignan; Jean-Pierre Lecouve, Caluire, all of France

[73] Assignee: Rhone-Poulenc Sante, Courbevoie, France

[21] Appl. No.: 167,488

[22] Filed: Mar. 14, 1988

Related U.S. Application Data

[62] Division of Ser. No. 24,677, Mar. 11, 1987.

[30] Foreign Application Priority Data

Mar. 14, 1986 [FR] France ............................... 86 03668

[51] Int. Cl.$^4$ ........................................... C07C 43/225
[52] U.S. Cl. .................................. 568/614; 568/615; 568/616
[58] Field of Search ......................... 568/616, 614, 604

[56] References Cited

U.S. PATENT DOCUMENTS 4,433,179  2/1984  Lohse et al. ....................... 568/616

Primary Examiner—Werren B. Lone
Attorney, Agent, or Firm—Stevens, Davis, Miller & Mosher

[57] ABSTRACT

Polyene aldehydes are made by reaction of a carbonyl compound of formula:

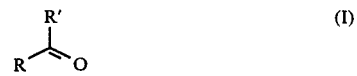

in which R denotes a hydrocarbon radical and R' denotes hydrogen or alkyl, with a metal derivative of a halogen compound of formula:

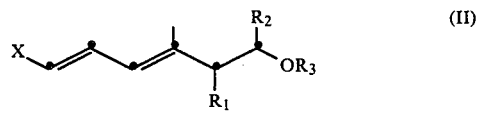

in which X denotes halogen (preferably bromine), $R_3$ is alkyl, and either $R_1$ denotes hydrogen and $R_2$ denotes an alkoxy radical indentical with $OR_3$ or $R_1$ and $R_2$ together form a bond, followed by hydrolysis of the product obtained.

2 Claims, No Drawings

PROCESS FOR THE PREPARATION OF POLYENE ETHERS

This is a division of application Ser. No. 024,677, filed Mar. 11, 1987.

The present invention relates to the preparation of polyene aldehydes of formula:

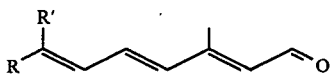 (I)

in which R denotes a hydrocarbon radical and R' denotes hydrogen or alkyl of 1 to 4 carbon atoms. Compounds of formula I of especial interest are those in which R' denotes methyl and R denotes methyl (dehydrocitral), 4,8-dimethyl-1,3,7-nonatrienyl (pseudo-retinal), or 2-(2,6,6-trimethyl-1-cyclohexenyl)ethenyl (retinal).

According to the present invention the compounds of formula (I) are prepared by reacting a carbonyl compound of the formula:

 (II)

in which R and R' are as defined above, with a metal derivative, prepared in situ by metal-halogen exchange, of a halogen compound of the formula:

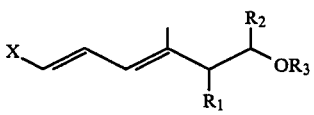 (III)

in which X denotes halogen (preferably bromine), $R_3$ denotes alkyl of 1 to 4 carbon atoms (preferably methyl or ethyl), and, either $R_1$ denotes hydrogen and $R_2$ denotes an alkoxy radical identical with $OR_3$, or $R_1$ and $R_2$ together form a bond, followed by hydrolysis of the product obtained.

The metal derivatives of the compound of formula (III) which are most suitable for the implementation of the present invention are the lithium, magnesium and copper derivatives. Lithium derivatives are of very special interest.

The metal derivatives of the compound of formula (III) may be prepared in situ by reaction of an organometallic derivative with a compound of formula (III), the operation being carried out in an anhydrous inert organic solvent, such as diethyl ether or tetrahydrofuran, at a temperature below $-50°$ C., and preferably in the region of $-70°$ C. It is particularly advantageous to use tert-butyllithium as the organometallic derivative.

The condensation of a carbonyl compound of formula (II) with the metal derivative of the compound of formula (III) may be performed in the same solvent at a temperature below $0°$ C., and generally below $-30°$ C.

Depending on the meanings of $R_1$, $R_2$ and $R_3$, the hydrolysis of the product obtained is performed with an inorganic acid (e.g. hydrochloric acid) in an aqueous organic medium (e.g. tetrahydrofuran-water or ethyl ether-water) at a temperature between $-60°$ C. and $+30°$ C. (when $R_1$ and $R_2$ denote a bond and $OR_3$ denotes alkoxy), or with an inorganic acid (e.g. hydrobromic acid) in an aqueous organic medium (e.g. acetone-water) at a temperature between $0°$ C. and the boiling temperature of the reaction mixture and, more particularly, under the conditions described in French Patent FR 78/24,350 (2,434,135) (when $R_1$ denotes hydrogen and $R_2$ and $OR_3$ both denote alkoxy).

The starting material of formula (III) in which $R_1$ denotes hydrogen and $R_2$ and $OR_3$ both denote alkoxy of 1 to 4 carbon atoms, may be obtained by reaction of a phosphonium halide, such as bromomethyltriphenylphosphonium bromide, with a 5,5-dialkoxy-3-methyl-2-pentenal, the reaction being carried out in the presence of an alkali metal alcoholate such as potassium tert-butylate, in an anhydrous organic solvent such as tetrahydrofuran, at a temperature between $-70°$ C. and $0°$ C.

The 5,5-dialkoxy-3-methyl-2-pentenal may be prepared according to the process described in French Patent FR 77/15,070 (2,391,181).

The starting materials of formula (III) in which $R_1$ and $R_2$ form a bond and $R_3$ denotes alkyl of 1 to 4 carbon atoms may be obtained by reaction of trimethylsilyl iodide in the presence of hexamethyldisilazane with a compound of formula (III) in which $R_1$ denotes hydrogen and $R_2$ denotes a radical $OR_3$ using the method described by R. D. Miller and D. R. McKean, Tetrahedron Letters 23, 323 (1982).

The compounds of formula (III) in which $R_1$ and $R_2$ form a bond and $R_3$ denotes alkyl of 1 to 4 carbon atoms are new and form another subject of the present invention.

The following Examples illustrate the present invention.

EXAMPLE 1

6-Bromo-3-methyl-1,1-dimethoxy-3,5-hexadiene (0.56 g; 2.38 mmol) dissolved in anhydrous ether (10 cc) is introduced, under an argon atmosphere, into a 25 cc 3-necked round flask fitted with a thermometer, a magnetic stirrer and a septum. After cooling to $-70°$ C., tert-butyllithium (2.4 cc, 1.8N in pentane, i.e. 1.8 equivalents) is added over 5 minutes while the temperature is kept below $-56°$ C. A temperature of $-70°$ C. is maintained for 70 minutes and a solution of β-ionone (0.33 g; 0.72 equivalent) in ether (4 cc) is then added. The temperature is allowed to rise to $0°$ C. over 15 minutes and is then maintained at this level for 1 hour 15 minutes. A 5% aqueous solution of sodium bicarbonate (3 cc) is then added. After 20 minutes' stirring at $0°$ C., the aqueous phase is extracted with ether and the ether phase is washed with water to neutrality and then dried over sodium carbonate. After filtration and evaporation of the solvents, a crude product (0.8 g) is obtained which is purified by flash chromatography on silica, eluting with a mixture of petroleum ether and diethyl ether (85/15 by volume).

9-(2,6,6-Trimethyl-1-cyclohexenyl)-1,1-dimethoxy-3,7-dimethyl-7-hydroxy-3,5,8-nonatriene, or $C_{20}$ dimethyl hydroxyacetal, (0.45 g) is obtained in this manner. The structure of the product is confirmed by the infrared spectrum and the proton nuclear magnetic resonance spectrum.

The following are introduced into a 100 cc 3-necked round flask fitted with a condenser, a septum and a magnetic stirrer:

$C_{20}$ dimethyl hydroxyacetal (0.9 g; 2.6 mmol),
a solution (60 cc) made from acetone (192 cc) and water (1 cc), Ionol (0.02 g), and
Water (0.2 cc).

These are refluxed (54° C.) for 5 minutes, and a solution (0.4 cc) of 48% aqueous hydrobromic acid (3 cc) in acetone (141 cc) is then added. The mixture is refluxed for 17 minutes and water (80 cc) is then added quickly. The contents are stirred for 10 minutes and then extracted with pentane. The organic phase is washed with 5% sodium bicarbonate solution, and then with water to a pH of about 7-8, and then dried over sodium carbonate. After filtration and evaporation of the solvent, the crude product obtained is purified by chromatography on silica, eluting with a mixture of petroleum ether and diethyl ether (98/2 by volume). Retainal (0.534 g) is obtained in this manner. The hydrolysuis yield is 72.7%.

6-Bromo-3-methyl-1,1-dimethoxy-3,5-hexadiene may be obtained in the following manner. Bromomethyltriphenylphosphonium bromide (12.24 g; 32.8 mmol) suspended in anhydrous tetrahydrofuran (160 cc) is introduced, under an argon atmosphere, in to a 500 cc 3-necked round flask fitted with a magnetic stirrer and a thermometer. After cooling to −70° C., potassium tert-butylate (3.15 g; 32.8 mmol) is added in small portions over 10 minutes. The mixture is stirred for 1 hour 30 minutes at −70° C. The white suspension becomes orange. 5,5-Dimethoxy-3-methyl-2-pentenal (3.3 g; 20.9 mmol i.e. 0.75 equivalent) dissolved in tetrahydrofuran (17 cc) is then added over 10 minutes at −70° C. The reactio mixture is kept for 1 hour at 0° C. and then for 1 hour 30 minutes at a temperature in the region of 20° C.

Water (85 cc) is quickly added and the mixture is then stirred vigorously for 10 minutes. The reaction mixture is taken up with ether (100 cc). After phase separation, the aqueous phase is extracted with ether (6×40 cc). The organic phases are dried over magnesium sulphate, filtered and evaporated. A viscous oil is obtained, to which sand (10 g) is added. After filtration through silica and elution with pentane, 6-bromo-2-methyl-1,1-dimethoxy-3,5-hexadiene (4.13 g) is obtained. The yield is 84%. The structure of the product obtained is confirmed by the infrared spectrum and the proton nuclear magnetic resonance spectrum.

EXAMPLE 2

The procedure is as in Example 1, but employs 6-bromo-3-methyl-1,1-diethoxy-3,5-hexadiene (0.56 g; 2.12 mmol) and β-ionone (0.33 g; 1.716 mmol, i.e. 0.8 equivalent). After flash chromatography, 9-(2,6,6-trimethyl-1cyclohexenyl)-1,1-diethoxy-3,7-dimethyl-7-hydroxy-3,5,8-nonatriene, or $C_{20}$ diethyl hydroxyacetal, (0.47 g) is obtained. The yield is 73%. The structure of the product obtained is confirmed by the infrared spectrum and the proton nuclear magnetic resonance spectrum.

A solution (30 cc) made from acetone (192 cc) and water (1 cc), $C_{20}$ diethyl hydroxyacetal (0.46 g; 1.22 mmol), Ionol (0.01 g), and water (0.1 cc) are introduced into a 50 cc 3-necked round flask fitted with a condenser, a septum and a magnetic stirrer. After refluxing (at 54° C.) for 5 minutes, a solution (0.2 cc) of 48% aqueous hydrobromic acid (3 cc) in acetone (141 cc) is added. Refluxing is continued for 17 minutes and water (40 cc) is then added quickly. The mixture is stirred for 10 minutes and then extracted with pentane. The organic phase is washed with 5% sodium bicarbonate solution and then with water to a pH of 7-8 and is finally dried over sodium carbonate. After filtration and evaporation of the solvent, the crude product is chromatographed on silica, eluting with a mixture of petroleum ether and diethyl ether (98/2 by volume). Retinal (0.25 g) is obtained in this manner. The yield is 72%.

6-Bromo-3-methyl-1,1-diethoxy-3,5-hexadiene is prepared under the conditions described earlier for the preparation of 6-bromo-3-methyl-1,1-dimethoxy-3,5-hexadiene. Starting with 5,5-diethoxy-3-methyl-2-pentenal (4.67 g; 25.1 mmol), 6-bromo-3-methyl-1,1-diethoxy-3,5-hexadiene (5.1 g) is obtained in 77.5% yield. The structure of the product obtained is confirmed by the infrared spectrum and the proton nuclear magnetic resonance spectrum.

EXAMPLE 3

By proceeding as in Example 1, but starting with 6-bromo-3-methyl-1,1-diethoxy-3,5-hexadiene (0.43 g; 1.63 mmol) and an excess of acetone (0.4 g i.e. 4 equivalents), 1,1-diethoxy-3,7-dimethyl-7-hydroxy-3,5-octadiene, or $C_{10}$ diethyl hydroxyacetal, (0.4 g) is obtained. After hydrolysis and purification by flash chromatography, eluting with a mixture of petroleum ether and diethyl ether (96/4 by volume), this compound yields dehydrocitral (0.121 g). The yield is 49.6%, based on the 6-bromo-3-methyl-1,1-diethoxy-3,5-hexadiene employed. The structure of the product obtained is confirmed by the infrared spectrum and the proton nuclear magnetic resonance spectrum.

EXAMPLE 4

The procedure is an in Example 3, but starting with 6-bromo-3-methyl-1,1-dimethoxy-3,5-hexadiene (0.56 g; 2.38 mmol) and an excess of acetone (0.4 g, i.e. 4 equivalents). After flash chromatography, eluting with a mixture of petroleum ether and diethyl ether (70/30 by volume), 1,1-dimethoxy-3,7-dimethyl-7-hydroxy-3,5-octadiene, or $C_{10}$ dimethyl hydroxyacetal, (0.44 g) is obtained. The yield is 86.8%.

$C_{10}$ Dimethyl hydroxyacetal obtained in this manner may be hydrolysed to give dehydrocitral (0.21 g), identical to that obtained in Example 3, in 60.2% yield.

EXAMPLE 5

The procedure is as in Example 1, but starting with 6-bromo-3-methyl-1,1-dimethoxy-3,5-hexadiene (0.55 g; 2.38 mmol) and pseudoionone (0.37 g; 1.90 mmol i.e. 0.8 equivalent). In this manner, after flash chromatography eluting with a mixture of petroleum ether and diethyl ether (80/20 by volume), 1-1-dimethoxy-3,7,11,15-tetramethyl-7-hydroxy-3,5,8,10,14-hexadecapentaene, or $C_{20}$ dimethyl hydroxyacetal, (0.60 g) is obtained. The yield is 87.8%.

The dimethyl hydroxyacetal obtained in this manner may be hydrolysed to give 3,7,11,15-tetramethyl-2,4,6,8,10,14-hexadecahexaenal, or pseudoretinal, (0.33 g) in 60.8% yield. The structure of the product obtained is confirmed by the infrared spectrum and the proton nuclear magnetic resonance spectrum.

EXAMPLE 6

6-Bromo-3-methyl-1-methoxy-1,3,5-hexatriene (0.257 g; 1.26 mmol) dissolved in ether (10 cc) is introduced, under an argon atmosphere, into a 25 cc round flask fitted with a thermometer and a magnetic stirrer. The flask is cooled to −70° C. tert-Butyllithium (1.2 cc, 1.8N in pentane; 2.1 mmol, i.e. 1.7 equivalent) is then added over 7 minutes while the temperature is kept below −68° C. The solution becomes slightly coloured from pale yellow to light chestnut-brown. It is stirred for 90 minutes at −70° C. β-Ionone (0.23 g; 1.196 mmol, i.e. 0.85 equivalent) dissolved in ether (3 cc) is then added. The mixture is stirred for 90 minutes at −30° C. 1N hydrochloric acid (4.5 cc) is added at −60° C. and the mixture is then stirred vigorously for 1 hour at 10° C. After phase separation, extraction with ether and evaporation of the solvent, a crude product (0.44 g) is obtained, which is purified by flash chromatography on silica, eluting with a mixture of petroleum ether and diethyl ether (98/2 by volume). Retinal (0.187 g) is obtained in this manner in 55% yield. The structure of the product is confirmed by the infrared spectrum and the proton nuclear magnetic resonance spectrum.

6-Bromo-3-methyl-1-methoxy-1,3,5-hexatriene may be prepared as follows. 6-Bromo-3-methyl-1,1-dimethoxy-3,5-hexadiene (1.17 g; 4.97 mmol) dissolved in carbon tetrachloride (10 cc) is introduced, under an argon atmosphere, into a 25 cc round flask. This is cooled to −10° C., and then hexamethyldisilazane (1.31 cc), followed by trimethylsilyl iodide (0.81 cc) are added. The mixture is left for 2 hours at 0° C., and its temperature is then allowed to rise to about 20° C. and is kept like this for 12 hours. The reaction mixture is taken up with pentane (50 cc), and the extract is filtered and the residue is washed with pentane. The pentane phase is washed with saturated sodium carbonate solution (4×3 cc). The brown solution becomes golden yellow. The organic phase is dried over sodium carbonate for 2 hours at 8° C. After quick filtration, the solvent is evaporated under reduced pressure (15 mm Hg; 2 kPa), with stirring and in the presence of sodium carbonate. When only 2 cc of solution remain, the 6-bromo-3-methyl-1-methoxy-1,3,5-hexatriene is distilled over sodium carbonate. In this manner, 6-bromo-3-methyl-1-methoxy-1,3,5-hexatriene (0.597 g) is obtained in 59.1% yield (b.p. 0.022 kPa=80° C.).

EXAMPLE 7

6-Bromo-3-methyl-1,1-dimethoxy-3,5-hexadiene (0.5 g; 2.12 mmol) dissolved in anhydrous tetrahydrofuran (10 cc) is introduced, under an argon atmosphere, into a 25 cc round flask fitted with a thermometer and a magnetic stirrer. After cooling to −70° C., tert-butyllithium (2.1 cc, 1.8N in pentane, i.e. 1.8 equivalent) is added over 7 minutes while the temperature is kept below −65° C. It is then maintained at −70° C. for 70 mnutes. Benzaldehyde (0.186 g; 0.8 equivalent) dissolved in tetrahydrofuran (4 cc) is then added. A temperature of about 20° C. is maintained for 40 minutes. A 5% aqueous solution of sodium bicarbonate (3 cc) is then added. After 1 hour's stirring at about 20° C., the reaction mixture is taken up with ether (50 cc). After phase separation, the aqueous phase is extracted with ether. The combined organic phases are washed with water to neutrality and then dried over sodium carbonate.

After filtration and evaporation of the solvents, 1,1-dimethoxy-3-methyl-7-phenyl-7-hydroxy-3,5-heptadiene (0.5 g) is obtained. The yield is quantitative.

3-Methyl-7-phenyl-2,4,6-heptatrienal is obtained by hydrolysing the hydroxyacetal obtained under the usual conditions.

We claim:

1. A compound of the formula:

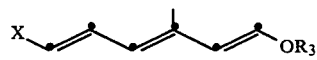

in which X is halogen and $R_3$ is alkyl of 1 to 4 carbon atoms.

2. A compound according to claim 1 which is 6-bromo-3-methyl-1-methoxy-1,3,5-hexatriene.

* * * * *